(12) United States Patent
Zhao

(10) Patent No.: US 9,527,617 B2
(45) Date of Patent: Dec. 27, 2016

(54) PACKAGING SOLUTIONS

(71) Applicant: Bausch & Lomb Incorporated, Rochester, NY (US)

(72) Inventor: Fang Zhao, Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 826 days.

(21) Appl. No.: 13/917,734

(22) Filed: Jun. 14, 2013

(65) Prior Publication Data

US 2013/0276407 A1  Oct. 24, 2013

Related U.S. Application Data

(62) Division of application No. 11/876,862, filed on Oct. 23, 2007, now Pat. No. 8,490,782.

(51) Int. Cl.
| | |
|---|---|
| *B65B 55/02* | (2006.01) |
| *C08F 220/36* | (2006.01) |
| *C08L 43/02* | (2006.01) |
| *C08F 230/02* | (2006.01) |
| *A61L 12/00* | (2006.01) |
| *G02B 1/04* | (2006.01) |
| *C08F 220/28* | (2006.01) |
| *B65B 25/00* | (2006.01) |

(52) U.S. Cl.
CPC ............. *B65B 55/02* (2013.01); *A61L 12/00* (2013.01); *C08F 220/36* (2013.01); *C08F 230/02* (2013.01); *C08L 43/02* (2013.01); *G02B 1/043* (2013.01); *B65B 25/008* (2013.01); *C08F 2220/282* (2013.01)

(58) Field of Classification Search
None
See application file for complete search history.

(56) References Cited

U.S. PATENT DOCUMENTS

| | | | |
|---|---|---|---|
| 3,408,429 A | 10/1968 | Wichterle | |
| 3,660,545 A | 5/1972 | Wichterle | |
| 4,113,224 A | 9/1978 | Clark et al. | |
| 4,136,250 A | 1/1979 | Mueller et al. | |
| 4,153,641 A | 5/1979 | Deichert et al. | |
| 4,197,266 A | 4/1980 | Clark et al. | |
| 4,740,533 A | 4/1988 | Su et al. | |
| 4,910,277 A | 3/1990 | Bambury et al. | |
| 4,954,587 A | 9/1990 | Mueller | |
| 5,010,141 A | 4/1991 | Mueller | |
| 5,034,461 A | 7/1991 | Lai et al. | |
| 5,070,215 A | 12/1991 | Bambury et al. | |
| 5,079,319 A | 1/1992 | Mueller | |
| 5,260,000 A | 11/1993 | Nandu et al. | |
| 5,271,875 A | 12/1993 | Appleton et al. | |
| 5,310,779 A | 5/1994 | Lai | |
| 5,321,108 A | 6/1994 | Kunzler et al. | |
| 5,358,995 A | 10/1994 | Lai et al. | |
| 5,387,662 A | 2/1995 | Kunzler et al. | |
| 5,431,879 A * | 7/1995 | Heyl | A45C 11/005 134/901 |
| 6,440,366 B1 * | 8/2002 | Salpekar | A61L 12/08 134/42 |
| 6,858,218 B2 | 2/2005 | Lai et al. | |
| 2004/0079922 A1 * | 4/2004 | Yokokouji | C09K 19/14 252/299.64 |
| 2006/0217276 A1 | 9/2006 | Mitani et al. | |
| 2007/0149428 A1 * | 6/2007 | Ammon, Jr. | A45C 11/005 510/112 |
| 2007/0286767 A1 * | 12/2007 | Burke | A61K 9/0048 422/28 |
| 2008/0095754 A1 * | 4/2008 | Burke | A61K 9/0048 424/94.61 |
| 2008/0141628 A1 * | 6/2008 | Lang | A61L 12/04 53/431 |
| 2008/0148689 A1 * | 6/2008 | Xia | A45C 11/005 53/431 |
| 2008/0197324 A1 * | 8/2008 | Zhao | C08K 5/0058 252/380 |
| 2008/0214421 A1 * | 9/2008 | Zhao | A01N 37/12 510/112 |
| 2008/0241225 A1 * | 10/2008 | Hill | A61K 9/0051 424/429 |
| 2008/0314767 A1 * | 12/2008 | Lai | A61L 12/086 206/5.1 |
| 2009/0100801 A1 * | 4/2009 | Zhao | A61L 12/00 53/425 |
| 2009/0156741 A1 * | 6/2009 | Suda | A61F 2/16 525/61 |
| 2014/0096484 A1 * | 4/2014 | Pruitt | G02B 1/043 53/425 |

FOREIGN PATENT DOCUMENTS

| | | |
|---|---|---|
| WO | WO 9631792 | 10/1996 |
| WO | WO 0215911 A1 | 2/2002 |

* cited by examiner

*Primary Examiner* — Hemant M Desai
*Assistant Examiner* — Mobeen Ahmed
(74) *Attorney, Agent, or Firm* — John E. Thomas

(57) ABSTRACT

A packaging system for the storage of an ionic, hydrogel contact lens employs an aqueous packaging solution including a phosphorylcholine polymer. Preferably, the solution has an osmolality of at least about 200 mOsm/kg, a pH of about 6 to about 8 and is heat sterilized.

13 Claims, No Drawings

PACKAGING SOLUTIONS

CROSS-REFERENCE TO RELATED APPLICATIONS

This application is a divisional of application Ser. No. 11/876,862, filed Oct. 23, 2007, which is incorporated by reference herein.

BACKGROUND OF THE INVENTION

1. Technical Field

The present invention generally relates to packaging solutions for contact lenses.

2. Description of Related Art

Blister-packs and glass vials are typically used to individually package each soft contact lens for sale to a customer. Saline or deionized water is commonly used to store the lens in the blister-packs, as mentioned in various patents related to the packaging or manufacturing of contact lenses. Because lens material may tend to stick to itself and to the lens package, packaging solutions for blister-packs have sometimes been formulated to reduce or eliminate lens folding and sticking. For this reason, polyvinyl alcohol (PVA) has been used in contact lens packaging solutions. Additionally, U.S. Pat. No. 6,440,366 discloses contact lens packaging solutions comprising polyethylene oxide (PEO)/polypropylene oxide (PPO) block copolymers, especially poloxamers or poloxamines.

It is highly desirable that contact lenses be as comfortable as possible for wearers. Manufacturers of contact lenses are continually working to improve the comfort of the lenses. Nevertheless, many people who wear contact lenses still experience dryness or eye irritation throughout the day and particularly towards the end of the day. An insufficiently wetted lens at any point in time will cause significant discomfort to the lens wearer. Although wetting drops can be used as needed to alleviate such discomfort, it would certainly be desirable if such discomfort did not arise in the first place.

Accordingly, it would be desirable to provide an improved packaging system for contact lenses such that the lenses would be comfortable to wear in actual use and allow for extended wear of the lenses without irritation or other adverse effects to the cornea.

SUMMARY OF THE INVENTION

In accordance with one embodiment of the present invention, this invention provides a packaging system for the storage of a contact lens comprising a sealed container that contains an unused, ionic contact lens in an aqueous packing solution. The packaging solution comprises a phosphorylcholine polymer, and has an osmolality of at least about 200 mOsm/kg and a pH in the range of about 6 to about 8.

The contact lens may be made of a silicone hydrogel copolymeric material. Preferably, the solution does not contain an effective disinfecting amount of a disinfecting agent. The phosphorylcholine polymer may comprise a copolymer of a phosphorylcholine comonomer and a second comonomer, such as a copolymer of a phosphorylcholine (meth)acrylate and an alkyl(meth)acrylate.

The concentration of the phosphorylcholine polymer in the solution is preferably about 0.001 to about 10% w/w, more preferably 0.01 to 2% w/w, most preferably 0.01 to 1% w/w. The solution may further comprise various other materials, such as a non-ionic surfactant, a buffering agent, and/or a non-ionic polymer.

In accordance with a second embodiment of the present invention, a method of preparing a package comprising a storable, sterile contact lens, comprises: (a) immersing an ionic contact lens in a solution comprising a phosphorylcholine polymer, wherein the solution has an osmolality of at least about 200 mOsm/kg and a pH in the range of about 6 to about 8; (b) packaging the solution and the device in a manner preventing contamination of the lens by microorganisms; and (c) sterilizing the packaged solution and device, preferably by heat sterilization.

Contact lenses, upon removal from the packaging system of this invention, are more comfortable to wear in actual use.

DETAILED DESCRIPTION OF THE PREFERRED EMBODIMENTS

The present invention provides a packaging system for the storage of contact lenses. These lenses can provide optical correction, wound care, drug delivery, diagnostic functionality or cosmetic enhancement or effect or a combination of these properties. The invention is applicable to soft, hydrogel contact lenses. As is understood by one skilled in the art, a lens is considered to be "soft" if it can be folded back upon itself without breaking. The invention is applicable to hydrogel contact lenses made of an ionic material in US FDA category III or IV. Category IV contact lenses are composed of at least 50 weight percent water when hydrated and are made of an ionic material. Category III contact lenses have a lower water content but are also made of an ionic material. Category I and II contact lenses, in contrast, are made of a non-ionic material.

Any material known to produce a Category III or IV hydrogel contact lens can be used herein. Hydrogels in general are a well-known class of materials that comprise hydrated, cross-linked polymeric systems containing water in an equilibrium state. Hydrogels generally have a water content greater than about 5 weight percent and more commonly between about 10 to about 80 weight percent. Hydrogels are generally prepared by polymerizing a monomeric mixture including at least one hydrophilic monomer; either one of the hydrophilic monomers functions as a crosslinking agent, or a separate crosslinking monomer may be employed in this monomeric mixture. (A crosslinker, crosslinking agent or crosslinking monomer is defined as a monomer having multiple polymerizable functionalities.) For ionic hydrogels, the initial monomeric mixture includes at least one ionic monomer. Silicone hydrogels are specific class of hydrogel materials which are usually prepared by polymerizing a monomeric mixture containing at least one silicone-containing monomer and at least one hydrophilic monomer; either the silicone-containing monomer or the hydrophilic monomer functions as a crosslinking agent, or a separate crosslinking monomer may be employed.

Suitable hydrophilic monomers include: amides such as dimethylacrylamide and dimethylmethacrylamide; cyclic lactams such as n-vinyl-2-pyrrolidone; poly(alkylene glycols) functionalized with polymerizable groups; carboxylic acids such as methacrylic acid, acrylic acid and N-vinyloxycarbonylanaline; and hydroxyalkyl monomers, such as 2-hydroxyethyl methacrylate; and oxazolone monomers, including those disclosed in U.S. Pat. No. 4,910,277. Other suitable hydrophilic monomers will be apparent to one skilled in the art. The carboxylic acid-containing monomers are examples of ionic, hydrophilic monomers.

Applicable silicone-containing monomeric units for use in the formation of silicone hydrogels are well known in the art and numerous examples are provided in U.S. Pat. Nos. 4,136,250; 4,153,641; 4,740,533; 5,034,461; 5,070,215; 5,260,000; 5,310,779, and 5,358,995.

Representative examples of applicable silicone-containing monomeric units include bulky polysiloxanylalkyl (meth)acrylic monomers. An example of a bulky polysiloxanylalkyl(meth)acrylic monomer is represented by the structure of Formula I:

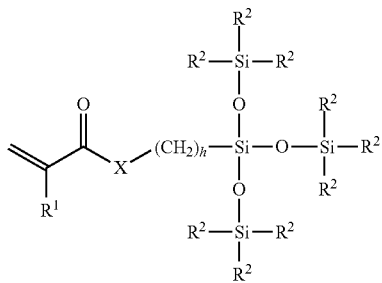

(I)

wherein X denotes —O— or —NR—; each $R^1$ independently denotes hydrogen or methyl; each $R^2$ independently denotes a lower alkyl radical, phenyl radical or a group represented by

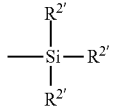

wherein each $R^{2'}$ independently denotes a lower alkyl or phenyl radical; and h is 1 to 10.

Examples of bulky monomers are methacryloxypropyl tris(trimethyl-siloxy)silane or tris(trimethylsiloxy)silylpropyl methacrylate, sometimes referred to as TRIS and tris (trimethylsiloxy)silylpropyl vinyl carbamate, sometimes referred to as TRIS-VC and the like.

Such bulky monomers may be copolymerized with a silicone macromonomer, which is a poly(organosiloxane) capped with an unsaturated group at two or more ends of the molecule. U.S. Pat. No. 4,153,641 discloses, for example, various unsaturated groups such as acryloxy or methacryloxy groups.

Another class of representative silicone-containing monomers includes, but is not limited to, silicone-containing vinyl carbonate or vinyl carbamate monomers such as, for example, 1,3-bis[4-vinyloxycarbonyloxy)but-1-yl]tetramethyl-disiloxane; 3-(trimethylsilyl)propyl vinyl carbonate; 3-(vinyloxycarbonylthio)propyl-[tris(trimethylsiloxy)silane]; 3-[tris(trimethylsiloxy)silyl]propyl vinyl carbamate; 3-[tris(trimethylsiloxy)silyl]propyl allyl carbamate; 3-[tris (trimethylsiloxy)silyl]propyl vinyl carbonate; t-butyldimethylsiloxyethyl vinyl carbonate; trimethylsilylethyl vinyl carbonate; trimethylsilylmethyl vinyl carbonate and the like and mixtures thereof.

Another class of silicone-containing monomers includes polyurethane-polysiloxane macromonomers (also sometimes referred to as prepolymers), which may have hard-soft-hard blocks like traditional urethane elastomers. They may be end-capped with a hydrophilic monomer such as 2-hydroxyethyl methacrylate (HEMA). Examples of such silicone urethanes are disclosed in a variety of publications, including U.S. Pat. No. 6,858,218 and PCT Published Application No. WO 96/31792, which disclosures are hereby incorporated by reference in their entirety. Further examples of silicone urethane monomers are represented by Formulae II and III:

$$E(*D*A*D*G)_a*D*A*D*E'; \text{or} \qquad (II)$$

$$E(*D*G*D*A)_a*D*A*D*E'; \text{or} \qquad (III)$$

wherein:

D independently denotes an alkyl diradical, an alkyl cycloalkyl diradical, a cycloalkyl diradical, an aryl diradical or an alkylaryl diradical having 6 to about 30 carbon atoms;

G independently denotes an alkyl diradical, a cycloalkyl diradical, an alkyl cycloalkyl diradical, an aryl diradical or an alkylaryl diradical having 1 to about 40 carbon atoms and which may contain ether, thio or amine linkages in the main chain;

* denotes a urethane or ureido linkage;

a is at least 1;

A independently denotes a divalent polymeric radical of Formula IV:

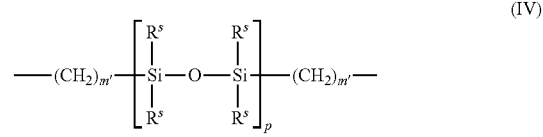

(IV)

wherein each $R^S$ independently denotes an alkyl or fluoro-substituted alkyl group having 1 to about 10 carbon atoms which may contain ether linkages between the carbon atoms; m' is at least 1; and p is a number that provides a moiety weight of about 400 to about 10,000;

each of E and E' independently denotes a polymerizable unsaturated organic radical represented by Formula V:

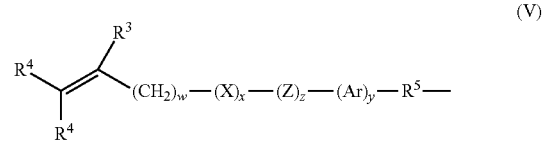

(V)

wherein:

$R^3$ is hydrogen or methyl;

$R^4$ is hydrogen, an alkyl radical having 1 to 6 carbon atoms, or a —CO—Y—$R^6$ radical wherein Y is —O—, —S— or —NH—;

$R^5$ is a divalent alkylene radical having 1 to about 10 carbon atoms;

$R^6$ is a alkyl radical having 1 to about 12 carbon atoms;

X denotes —CO— or —OCO—;

Z denotes —O— or —NH—;

Ar denotes an aromatic radical having about 6 to about 30 carbon atoms;

w is 0 to 6; x is 0 or 1; y is 0 or 1; and z is 0 or 1.

A specific example of a silicone-containing urethane monomer is represented by Formula VI:

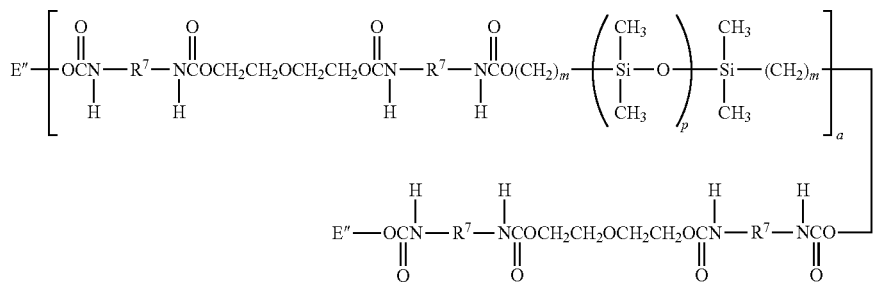

wherein m is at least 1 and is preferably 3 or 4, a is at least 1 and preferably is 1, p is a number which provides a moiety weight of about 400 to about 10,000 and is preferably at least about 30, $R^7$ is a diradical of a diisocyanate after removal of the isocyanate group, such as the diradical of isophorone diisocyanate, and each E" is a group represented by:

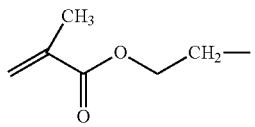

In another embodiment of the present invention, a silicone hydrogel material comprises (in bulk, that is, in the monomer mixture that is copolymerized) about 5 to about 50 percent, and preferably about 10 to about 25, by weight of one or more silicone macromonomers, about 5 to about 75 percent, and preferably about 30 to about 60 percent, by weight of one or more polysiloxanylalkyl(meth)acrylic monomers, and about 10 to about 50 percent, and preferably about 20 to about 40 percent, by weight of a hydrophilic monomer, wherein at least one of the hydrophilic monomers is an ionic monomer.

The above silicone materials are merely exemplary, and other materials for use as substrates that can benefit by being packaged in the packaging solution according to the present invention and have been disclosed in various publications and are being continuously developed for use in contact lenses and other medical devices can also be used. For example, an ophthalmic lens for use herein can be a cationic lens such as a cationic contact lens or fluorinated silicone-containing monomers. Such monomers have been used in the formation of fluorosilicone hydrogels to reduce the accumulation of deposits on contact lenses made therefrom, as disclosed in, for example, U.S. Pat. Nos. 4,954,587; 5,010,141 and 5,079,319. The use of silicone-containing monomers having certain fluorinated side groups, i.e., —($CF_2$)—H, have been found to improve compatibility between the hydrophilic and silicone-containing monomeric units. See, e.g., U.S. Pat. Nos. 5,321,108 and 5,387,662.

Contact lenses for application of the present invention can be manufactured employing various conventional techniques, to yield a shaped article having the desired posterior and anterior lens surfaces. Spincasting methods are disclosed in U.S. Pat. Nos. 3,408,429 and 3,660,545; static casting methods are disclosed in U.S. Pat. Nos. 4,113,224, 4,197,266, and 5,271,875.

Next, the lens will be immersed in a packaging solution and stored in a packaging system according to the present invention. Generally, a packaging system for the storage of a contact lens according to the present invention includes at least a sealed container containing an unused contact lens immersed in an aqueous lens packaging solution. Preferably, the sealed container is a hermetically sealed blister-pack, in which a concave well containing a contact lens is covered by a metal or plastic sheet adapted for peeling in order to open the blister-pack. The sealed container may be any suitable generally inert packaging material providing a reasonable degree of protection to the lens, preferably a plastic material such as polyalkylene, PVC, polyamide, and the like.

Any suitable phosphorylcholine polymer may be employed in the packaging solution of this invention provided that it functions as described herein and has no substantial detrimental effect on the contact lens being stored or on the wearer of the contact lens. This component is ophthalmically acceptable at the concentrations used. Particularly useful components are those, which are water soluble, for example, soluble at the concentrations used in the presently useful liquid aqueous media.

It is believed these polymers enhance initial and extended comfort when a contact lens, packaged in the solution and then removed from the packaging system, is placed on the eye for wearing.

The phosphorylcholine polymer may comprise a copolymer of a phosphorylcholine comonomer and a second comonomer. Examples of such copolymers include a copolymer of a phosphorylcholine(meth)acrylate and a (C1-C25) alkyl(meth)acrylate. (As used herein, the term "(meth)" denotes optional methyl substitution. Thus, a term such as "(meth)acrylate" denotes acrylate or methacrylate.) A specific example is a copolymer of 2-methacryloyloxyethyl phosphorylcholine and n-butyl methacrylate. Such materials are commercially available under the tradenames Purebright and Lipidure. When a copolymer is employed, it is preferred the phosphorylcholine moiety constitutes at least 40 wt % of the copolymer. The phoshorylcholine polymer is present in the solution at about 0.001 to about 10% w/w, more preferably 0.01 to 2% w/w.

Various other materials may be included in the packaging system.

A surfactant may be included in the aqueous solution. Preferred are non-ionic surfactants, especially block copolymers of PEO and PPO. This class includes poloxamers and poloxamines, including those disclosed in U.S. Pat. No. 6,440,366. When present, the surfactant is employed at a concentration from about 0.01 to about 10% w/w and preferably from about 0.5 to about 1.5% w/w.

A polymeric conditioning agent may be included in the aqueous solution. One class includes nonionic polysaccharides, such as methylcellulose; hydroxyethylcellulose; hydroxypropylcellulose; hydroxypropylmethylcellulose; and methylhydroxyethyl starches. Another class of nonionic, polymeric conditioning agents includes polyvinylalcohols and polyvinylpyrrolidones. When present, the conditioning agent is employed at a concentration from about 0.01 to about 10% w/w and preferably from about 0.5 to about 1.5% w/w.

The packaging solutions according to the present invention are physiologically compatible. Specifically, the solution must be "ophthalmically safe" for use with a lens such as a contact lens, meaning that a contact lens treated with the solution is generally suitable and safe for direct placement on the eye without rinsing, that is, the solution is safe and comfortable for daily contact with the eye via a contact lens that has been wetted with the solution. An ophthalmically safe solution has a tonicity and pH that is compatible with the eye and includes materials, and amounts thereof, that are non-cytotoxic according to ISO standards and U.S. Food & Drug Administration (FDA) regulations. The solution should be sterile in that the absence of microbial contaminants in the product prior to release must be statistically demonstrated to the degree necessary for such products. The liquid media useful in the present invention are selected to have no substantial detrimental effect on the lens being treated or cared for and to allow or even facilitate the present lens treatment or treatments. The liquid media are preferably aqueous-based. A particularly useful aqueous liquid medium is that derived from saline, for example, a conventional saline solution or a conventional buffered saline solution.

The pH of the present solutions should be maintained within the range of about 6.0 to about 8, and preferably about 6.5 to about 7.8. Suitable buffers may be added, such as: phosphate; borate; citrate; carbonate; tris-(hydroxymethyl)aminomethane (TRIS); bis(2-hydroxyethyl)-iminotris-(hydroxymethyl)aminoalcohol (bis-tris); zwitterionic buffers such as N-[2-Hydroxy-1,1-bis(hydroxymethyl)ethyl]glycine (Tricine) and N-[2-Hydroxy-1,1-bis(hydroxymethyl)ethyl]glycine, MOPS; N-(Carbamoylmethyl)taurine (ACES); amino acids and amino acid derivatives; and mixtures thereof. Generally, buffers will be used in amounts ranging from about 0.05 to about 2.5 percent by weight, and preferably from about 0.1 to about 1.5 percent by weight of the solution.

If needed, the solutions of the present invention may be adjusted with tonicity agents, to approximate the osmotic pressure of normal lacrimal fluids, which is equivalent to a 0.9 percent solution of sodium chloride or 2.5 percent of glycerol solution. The solutions are made substantially isotonic with physiological saline used alone or in combination, otherwise if simply blended with sterile water and made hypotonic or made hypertonic the lenses will lose their desirable optical parameters. Correspondingly, excess saline may result in the formation of a hypertonic solution, which will cause stinging, and eye irritation.

Examples of suitable tonicity adjusting agents include, but are not limited to, sodium and potassium chloride, dextrose, calcium and magnesium chloride and the like and mixtures thereof. These agents are typically used individually in amounts ranging from about 0.01 to about 2.5% w/v and preferably from about 0.2 to about 1.5% w/v. Preferably, the tonicity agent will be employed in an amount to provide a final osmotic value of at least about 200 mOsm/kg, preferably from about 200 to about 450 mOsm/kg, more preferably from about 250 to about 400 mOsm/kg, and most preferably from about 280 to about 370 mOsm/kg.

If desired, one or more additional components can be included in the packaging solution. Such additional component or components are chosen to impart or provide at least one beneficial or desired property to the packaging solution. Such additional components may be selected from components that are conventionally used in one or more ophthalmic device care compositions. Examples of such additional components include cleaning agents, wetting agents, nutrient agents, sequestering agents, viscosity builders, contact lens conditioning agents, antioxidants, and the like and mixtures thereof. These additional components may each be included in the packaging solutions in an amount effective to impart or provide the beneficial or desired property to the packaging solutions. For example, such additional components may be included in the packaging solutions in amounts similar to the amounts of such components used in other, e.g., conventional, contact lens care products.

Useful sequestering agents include, but are not limited to, disodium ethylene diamine tetraacetate, alkali metal hexametaphosphate, citric acid, sodium citrate and the like and mixtures thereof.

Useful antioxidants include, but are not limited to, sodium metabisulfite, sodium thiosulfate, N-acetylcysteine, butylated hydroxyanisole, butylated hydroxytoluene and the like and mixtures thereof.

The method of packaging and storing an ophthalmic lens according to the present invention includes at least packaging the ophthalmic lens immersed in the aqueous contact lens packaging solution described above. The method may include immersing the ophthalmic lens in an aqueous contact lens solution prior to delivery to the customer/wearer, directly following manufacture of the contact lens. Alternately, the packaging and storing in the solution of the present invention may occur at an intermediate point before delivery to the ultimate customer (wearer) but following manufacture and transportation of the lens in a dry state, wherein the dry lens is hydrated by immersing the lens in the contact lens packaging solution. Consequently, a package for delivery to a customer may include a sealed container containing one or more unused contact lenses immersed in an aqueous contact lens packaging solution according to the present invention.

In one embodiment, the steps leading to the present ophthalmic device packaging system include (1) molding an ophthalmic device in a mold comprising at least a first and second mold portion, (2) removing the lens from the mold portions; (3) introducing the packing solution of this invention and the ophthalmic lens into the container, and (4) sealing the container. Preferably, the method also includes the step of sterilizing the contents of the container. Sterilization may take place prior to, or most conveniently after, sealing of the container and may be effected by any suitable method known in the art, e.g., by balanced autoclaving of the sealed container at temperatures of about 120° C. or higher. Preferred packages are plastic blister packages, including a recess for receiving a contact lens and the package solution, where the recess is sealed with lidstock prior to sterilization of the package contents.

The following examples are provided to enable one skilled in the art to practice the invention and are merely illustrative of the invention. The examples should not be read as limiting the scope of the invention as defined in the claims.

Example 1

A master batch solution was prepared by mixing 50 mg of a copolymer of 2-methacryloyloxytheyl phosphorylcholine and n-butyl methacrylate (MPC-BMA) in 50 mL of phosphate buffered saline (PBS, pH=7.4), to obtain a PBS solution with a concentration of 0.1 wt % MPC-BMA. The MPC-BMA was supplied by NOF America under the tradename Purebright MB-37-50T.

Two types of contact lenses were tested. The first contact lenses were PureVision™ contact lenses (Bausch & Lomb Incorporated), made of balatilicon A copolymer, a Group III contact lens. The second contact lenses were Oasys™ contact lenses (Johnson & Johnson Vision Care), made of senofilcon A copolymer, a Group II contact lens.

Summarized in Table 1, Treatment A of the contact lenses involved soaking the contact lenses 30 minutes in water, as a control. Treatment B involved soaking the contact lenses 20 hours in the MPC-BMA test solution, followed by soaking 30 minutes in water. Treatment C involved soaking the contact lenses 20 hours in the MPC-BMA test solution, followed by soaking 4 hours in water. Treatment D involved soaking the contact lenses 20 hours in the MPC-BMA test solution, followed by soaking 4 hours in 1M NaCl solution, followed by soaking 30 minutes in water. Phosphorus content on the lens surface was analyzed by XPS following the treatments. ND denotes not detected.

TABLE 1

|  | % Phosphorus (by XPS) | |
| --- | --- | --- |
|  | Balafilcon A | Senofilcon A |
| Treatment A | ND | ND |
| Treatment B | 0.3 ± 0.0 | 0.2 ± 0.0 |
| Treatment C | 0.2 ± 0.1 | ND |
| Treatment D | 0.2 ± 0.1 | ND |
| MCP-BMA Copolymer (solid) | 2.8 ± 0.1 | |

The MPC-BMA remained bound to the balafilcon A contact lenses, but not to the senofilcon A contact lenses, in Treatments C and D, indicating the phosphorylcholine polymer would be predicted to remain on the balafilcon A lens surface during at least early stages of wear of the contact lenses.

Example 2

Various tests were performed to assess the compatibility of the packaging solutions of this invention with the balafilcon A Group III contact lenses. The packaging solution included 0.1 wt % of the MPC-BMA copolymer of Example 1 in phosphate buffered saline (pH 7.2). The balafilcon A contact lenses were immersed in this packaging solution of Example 1 in glass vials. The packaged lens and solution were autoclaved for 30 minutes at 121° C.

Table 2 lists the contact lens dimensions after autoclaving, as well as target parameters. Table 3 lists the packaging solution properties before and after autoclaving. Both the contact lenses and packaging solution were sufficiently stable in these test regimens.

TABLE 2

| Lens Parameter | After Autoclave | Target |
| --- | --- | --- |
| Diameter | 14.08 ± 0.03 mm | 14.00 ± 0.20 mm |
| Saggital Depth | 3.68 ± 0.02 mm | 3.65 ± 0.10 mm |
| Center Thickness | 0.10 ± 0.00 mm | 0.09 ± 0.02 mm |
| Power | −3.00 ± 0.00 diopter | −3.00 ± 0.125 diopter |
| Cosmetic Appearance | (= to control) | — |

TABLE 3

| Solution Parameter | Before Autoclave | After Autoclave |
| --- | --- | --- |
| pH | 7.25 | 7.24 |
| Osmolality (mOsm/kg) | 246 | 247 |

Example 3

A first packaging solution was prepared by employing 0.01 wt % of the MPC-BMA copolymer of Example 1 in phosphate buffered saline (designated as Test Solution A below). A second packaging solution was prepared by employing 1 wt % of the MPC-BMA copolymer of Example 1 in phosphate buffered saline (designated as Test Solution B below). Commercial PureVision™ balafilcon A contact lenses (designated as Comparative Solution below), packaged in borate buffered saline, were used for comparative purposes. Balafilicon A contact lenses were soaked in the respective solutions for no fewer than 72 hours. Lenses were then removed from the test solution (and in the case of the comparative lenses, lenses were removed from the BBS packaging solution) and were immediately mounted and tested in 1 mL phosphate borate saline (PBS). Tribological testing was performed on a CETR Model UMT-2 micro-tribometer. Each lens was clamped on an HDPE holder that initially mates with the posterior side of the lens. A poly (propylene) clamping ring was then used to hold the edge region of the lens. Once the lens was mounted in the holder the assembly was placed in a stationary clamping device within the micro-tribometer. A polished stainless steel disc containing 1 mL of the test solution was then brought into contact with the lens and $F_N$ was adjusted to 2 grams over the course of the run for the frictional measurements. After the load equilibrated for 5 seconds the stainless steel disc was rotated at a velocity of 12 cm/sec for a duration of 20 sec in both the forward and reverse directions and the peak (static) and average (kinetic) COF values were recorded. Each value represents the average of 4-5 lenses. Controls were run from the same lot of lenses that were not subjected to any test solution. All data was normalized to the average values obtained from the lens holder in the absence of a lens tested in PBS. The results are summarized in Table 4. Packaging solution was prepared by employing 0.01 wt % of the MPC-BMA copolymer of Example 1 in phosphate buffered saline (designated as Test Solution A below).

TABLE 4

| Solution | Mean Static COF | Standard Error | Mean Kinetic COF | Standard Error |
| --- | --- | --- | --- | --- |
| Test Solution A | 2.535 | 0.941 | 0.252 | 0.032 |
| Test Solution B | 1.812 | 0.405 | 0.300 | 0.019 |
| Comparative Solution | 3.465 | 2.475 | 0.352 | 0.021 |

Tribology is the study of how two surfaces interact with each other when in relative motion. One aspect of tribology that may be of importance to contact lenses is friction. Friction is a measure of a material's resistance to lateral motion when placed against a specific substrate. The relative friction between two surfaces may be described in terms of a coefficient of friction (COF), which is defined as the ratio of the lateral force ($F_x$) that is required to initiate and then sustain movement to the normal force ($F_N$). Further, there are two friction coefficients that may be considered, the peak (or static) and average (or kinetic). The static COF is a measure of how much $F_x$ is needed to initiate relative motion of two surfaces and is typically the larger of the two values. Practically, for contact lenses, the static COF is related to the amount of force needed to start a blink cycle or for the lens to begin moving over the cornea. The kinetic COF is a measure of how much lateral force is needed to sustain movement at a particular velocity averaged over a finite period of time. This value is related to the amount of force required to sustain the blink over the course of the entire cycle and the ease of motion of the lens on the cornea (which may be further related to how much the lens moves on the cornea).

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A method of preparing a package comprising a storable, sterile contact lens, the method comprising:
   (a) immersing the contact lens in a solution comprising a phosphorylcholine polymer, wherein the contact lens is an ionic contact lens, wherein the phosphorylcholine polymer comprises a copolymer of a phosphorylcholine (meth)acrylate and an alkyl (meth)acrylate and further wherein the solution has an osmolality of at least about 200 mOsm/kg and a pH in the range of about 6 to about 8;
   (b) packaging the solution and the ionic contact lens in a manner preventing contamination of the lens by microorganisms; and
   (c) sterilizing the packaged solution and ionic contact lens.

2. The method of claim 1, wherein the contact lens is a silicone hydrogel contact lens.

3. The method of claim 1, wherein the phosphorylcholine polymer comprises a copolymer of 2-methacryloyloxyethyl phosphorylcholine and n-butyl methacrylate.

4. The method of claim 1, wherein the concentration of the phoshorylcholine polymer is about 0.001 to about 10% w/w.

5. The method of claim 1, wherein the solution further comprises a non-ionic surfactant.

6. The method of claim 5, wherein the non-ionic surfactant includes a polyethylene oxide (PEO)/polypropylene oxide (PPO) block copolymer.

7. The method of claim 1, wherein the solution further comprises a buffering agent.

8. The method of claim 7, wherein the buffering agent comprises at least one member selected from the group consisting of phosphate; boratecitrate; carbonate; TRIS; bis-tris; Tricine; MOPS; ACES; and an amino acid.

9. The method of claim 1, wherein the solution further comprises a non-ionic polymer.

10. The method of claim 9, wherein the non-ionic polymer includes at least one member selected from the group consisting of polyvinylalcohol, a cellulose-derived polymer and poly(N-vinyl pyrrolidinone).

11. The method of claim 1, including hermetically sealing the contact lens and the contact lens packing solution in the package and heat sterilizing the package contents.

12. The method of claim 1, wherein the solution does not contain an effective disinfecting amount of a disinfecting agent.

13. The method of claim 1, wherein the solution does not contain a germicide compound.

* * * * *